United States Patent [19]
Vogt et al.

[11] Patent Number: 6,048,458
[45] Date of Patent: *Apr. 11, 2000

[54] APPARATUS AND METHOD FOR WASTE RECYCLING AND CONVERSION

[75] Inventors: Gregory M. Vogt; Hubert S. Vogt; Herman K. Walter, all of Toronto, Canada

[73] Assignee: Eastern Power Limited, Toronto, Canada

[*] Notice: This patent is subject to a terminal disclaimer.

[21] Appl. No.: 09/126,436

[22] Filed: Jul. 30, 1998

Related U.S. Application Data

[63] Continuation-in-part of application No. 08/758,720, Nov. 29, 1996, Pat. No. 5,795,479.
[60] Provisional application No. 60/007,862, Dec. 1, 1995.

[51] Int. Cl.[7] .................................................. C02F 3/28
[52] U.S. Cl. .......................... 210/603; 210/612; 210/631; 210/769; 210/663; 210/912; 210/914; 435/262.5
[58] Field of Search ..................... 210/603, 612, 210/631, 768, 769, 774, 914, 912, 913, 663; 435/262, 262.5

[56] References Cited

U.S. PATENT DOCUMENTS

| | | | |
|---|---|---|---|
| 223,901 | 1/1880 | Fritz | 209/221 |
| 1,034,969 | 8/1912 | Brown, Jr. | 209/221 |
| 4,016,071 | 4/1977 | Paterson | 209/39 |
| 4,018,675 | 4/1977 | Petrucci | 209/86 |
| 4,185,680 | 1/1980 | Lawson | 162/5 |
| 4,274,838 | 6/1981 | Dole et al. | 210/612 |
| 4,302,236 | 11/1981 | Roman | 71/9 |
| 4,370,233 | 1/1983 | Hayes et al. | 210/609 |
| 4,429,043 | 1/1984 | Paton | 435/167 |
| 4,604,206 | 8/1986 | Sullivan | 210/603 |
| 4,758,344 | 7/1988 | Wildenauer | 210/603 |
| 4,824,571 | 4/1989 | Ducellier et al. | 210/603 |
| 4,826,602 | 5/1989 | Revis et al. | 210/914 |
| 4,846,975 | 7/1989 | Kelyman | 210/603 |
| 5,034,131 | 7/1991 | Stenroos et al. | 210/612 |
| 5,120,409 | 6/1992 | Hanulik | 205/105 R |
| 5,200,087 | 4/1993 | Nishihara | 210/914 |
| 5,282,938 | 2/1994 | Legiec et al. | 204/105 R |
| 5,377,917 | 1/1995 | Wiljan | 241/14 |
| 5,389,258 | 2/1995 | Smis et al. | 210/603 |
| 5,660,735 | 8/1997 | Coltrinari et al. | 210/769 |
| 5,795,479 | 8/1998 | Vogt et al. | 210/603 |

FOREIGN PATENT DOCUMENTS

| | | |
|---|---|---|
| 561731 | 9/1993 | European Pat. Off. . |
| 2652519 | 4/1991 | France . |
| 47-185 | 3/1968 | Japan . |
| 553891 | 3/1946 | United Kingdom . |

*Primary Examiner*—Christopher Upton
*Attorney, Agent, or Firm*—Ridout & Maybee

[57] ABSTRACT

Municipal solid waste is classified as to density as well as size in a perforated inclined trommel through which a gas stream is flowed inwardly through the perforations and downwardly to entrain aid remove paper and plastics through the lower end. Ferrous and non-ferrous metals are removed from the residue which is digested anaerobically in two stages with an intermediate steam explosion treatment to expose cellulose fibers coated with lignin. Mercury may be removed as a vapor phase in an initial stage of the steam heating and condensed and collected. An aqueous phase of the anaerobic digestate may be treated to remove heavy metals and may be discarded or reused to slurry solid phase incoming to a digester. The solids phase of the anaerobic digestate may be acidified to solubilize heavy metals which are recovered by electrodeposition from the solution. The depleted residue can be neutralized and disposed of.

35 Claims, 7 Drawing Sheets

APPARATUS AND METHOD FOR WASTE RECYCLING AND CONVERSION

CROSS-REFERENCE TO RELATED APPLICATIONS

This application is a continuation-in-part of patent application Ser. No. 08/758,720 filed Nov. 29, 1996 (issued as U.S. Pat. No. 5,795,479) that claims the benefit of prior filed provisional application No. 60/007,862 filed Dec. 1, 1995.

BACKGROUND OF THE INVENTION

The present invention relates to apparatus and methods adapted for use in waste recycling and conversion, more especially in association with the recycling and conversion of municipal solid waste (MSW) derived for example from domestic and commercial refuse or garbage.

Known apparatus and methods of which the applicant is aware are not as efficient as is desired, and are used in association with land filling and incineration which can lead to problems of toxic or hazardous air emissions and land pollution.

The apparatus and methods of the invention are especially although not exclusively adapted for use in association with waste management procedures which avoid the problems associated with land filling and incineration, as all the products are marketable, and there are no toxic or hazardous air emissions nor is there release of land pollutants.

BRIEF SUMMARY OF THE INVENTION

In one aspect, the present invention provides a trommel for classifying municipal solid waste (MSW) comprising an inclined cylindrical drum driven to rotate about its axis and having perforations in its side wall through which fragments conforming to a predetermined size range may fall, means for introducing MSW at an upper end of the drum, and means for inducing floor of a stream of gas inwardly through the perforations in said side wall and outwardly through the lower end of the drum to retain and remove relatively less dense materials through the lower end of the drum.

The trommel may advantageously be used as part of an initial stage of treatment of MSW. Whereas known trommels of which applicant is aware serve to classify materials only as to size, the present trommel also serves to classify materials according to the density of the components of the waste. For example, the stream of gas referred to serves to retain within the trommel and separate out relatively light weight materials such as paper and plastics to provide an output stream which can be treated in conventional manner to separate paper and plastics to provide saleable outputs of recycled paper and plastics, respectively.

A further advantage of the arrangement of the invention is that it avoids the need for air classifiers in later stages of the treatment and this reduces the energy requirements for operation of the system.

In a further aspect, the invention provides a method of digestion of MSW comprising digestible organic material and lignin coated cellulose fiber, comprising: heating the MSW in the presence of moisture to yield a heated solid phase; compressing and explosively decompressing the heated solid phase to yield a treated solid phase comprising the fibers in ruptured condition exposing the cellulosic internal surfaces thereof; slurrying the treated solid phase in an aqueous phase and subjecting the slurry to anaerobic digestion; and recovering a solid residue. The starting material MSW may itself have undergone a primary stage of anaerobic digestion before being subjected to explosive decompression to expose cellulosic fibers. Mercury, if present in the MSW may be distilled off and collected as the MSW is heated.

In a preferred form, the MSW material treated in this method comprises material that has undergone treatment in a trommel as described above and has been treated to remove paper, plastics, ferrous materials and aluminum and other non-ferrous metals, and hence is a principally organic substrate.

In accordance with further aspects of the invention, the digestate moves in a substantially straight line path through the digesters, and temperatures of the various zones of the digester are controlled by supply to these zones of a mixture of heated and unheated recirculated compressed digester gas.

In a preferred form, where tie MSW contains heavy metals, a portion of the aqueous phase containing dissolved heavy metals is removed from the digester before completion of the digestion, and heavy metals are removed from the aqueous phase. Various conventional treatments, for example application of reverse osmotic pressure membranes, separation membranes, chemical precipitation, or, more preferably, contacting the aqueous phase with a solid adsorbent may be used to remove the heavy metals. The resulting heavy metal poor aqueous phase may be discarded or may be utilized for slurrying solid phase digestible material that is fed to a digester.

Alternatively, or in a further heavy metals recovery step, heavy metals are recovered from anaerobically digested waste residue municipal solid waste containing lignin and heavy metals, by mixing the waste residue with mineral acid solution and obtaining a heavy metal salt solution containing heavy metal cations and lignin in solution and an insoluble residue; separating the solution from the insoluble residue; electrifying the separated solution, and causing electrodeposition of the heavy metal cations in the presence of the lignin to yield a heavy metal electrodeposit; and recovering the electrodeposit. The presence of lignin, preferably obtained as a residue from an anaerobic digestion procedure as described above, increases the efficiency of the plating out of the heavy metals.

In a further aspect, plastics residues remaining in the anaerobic digested material are recovered in the acidification step, wherein the specific gravity of the acid solution is sufficient to cause the plastics and any undigested organics to float on the surface of the acid solution, whereby they may be separated, for example by skimming them off.

BRIEF DESCRIPTION OF THE SEVERAL VIEWS OF THE DRAWINGS

The invention will be described in more detail, by way of example only, with reference to the accompanying drawings, wherein.

DETAILED DESCRIPTION OF THE INVENTION

Figure 1:
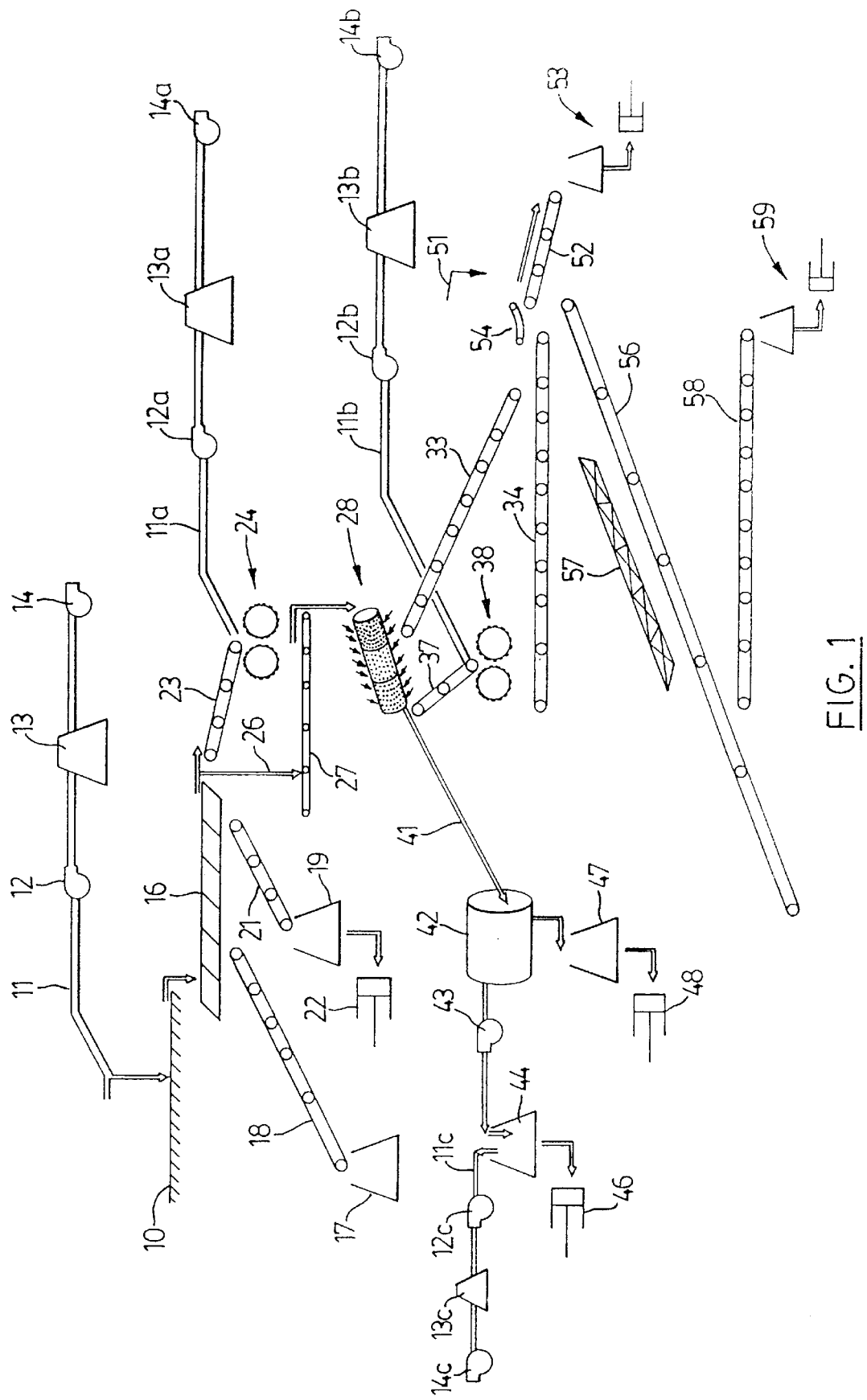
FIGS. 1, 2 and 3 illustrate partially schematically, in the nature of a flow sheet, successive stages of apparatus for use in carrying out a waste recycling and conversion process in accordance with the invention.

Referring to the drawings, wherein like reference numerals indicate like parts, FIG. 1 shows a first portion of a waste recycling and conversion process in accordance with the invention wherein municipal solid waste is tipped at a tipping floor 10, preferably in an enclosed environment wherein a negative pressure is maintained by withdrawing air along a line 11 through a fan or blower 12 feeding into a bag house filter 13 to a further fan 14, the output of which may be, for example, used as combustion air in, for example, a power plant (not shown) in association with which the process may preferably be operated.

The waste from the tipping floor 10 is fed by conveyor along a manual sorting line 16 from which large items are removed by operatives. Large pieces of ferrous metal are moved to a storage bin 17 by a conveyor 18 and large pieces of cardboard to a storage bin 19 by a conveyor 21 from which they may periodically be removed and compressed at a baler 22 for transport.

Adjacent the end of the manual sorting line 16 is a conveyor 23 that feeds the waste from the manual sorting 16 to a conventional form of bulk shredder 24. Small fragments of waste that do not require shredding may fall through a gap between the line 16 and 23, as indicated by arrow 26 and fall direct to a conveyor 27 which also receives the output from the shredder 24.

Figure 4:
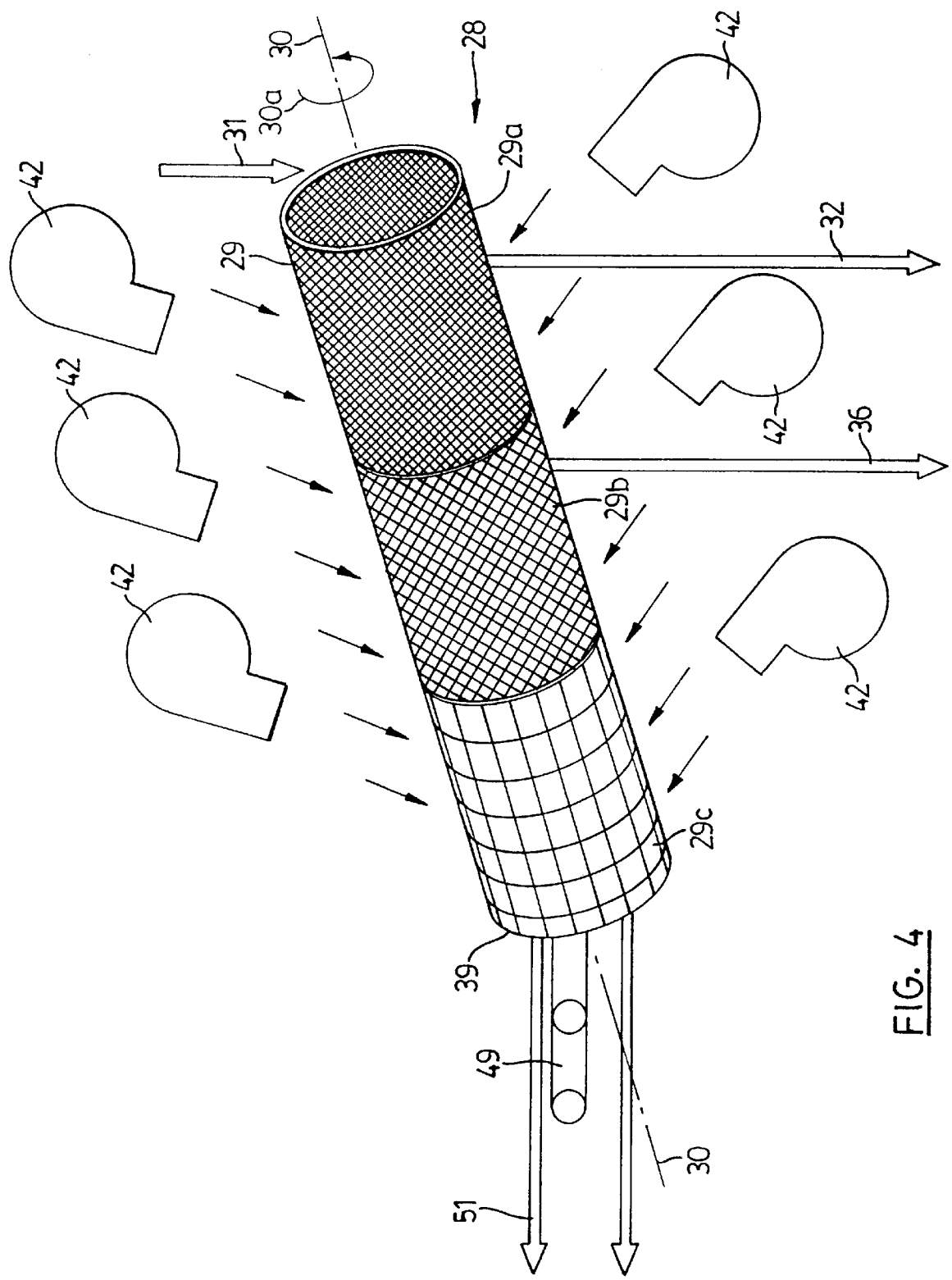
FIG. 4 shows on an enlarged scale a trommel in accordance with the invention preferably forming part of the apparatus of FIGS. 1 to 3.

The shredded waste is fed to a trommel 28 shown in more detail in FIG. 4.

The trommel 28 comprises a downwardly inclining cylindrical drum 29. The dimensions of the cylinder 29 depend upon the nature of the waste material, but in a typical example the cylinder 29 may be about 12 feet in diameter and about 70 feet long. Its side wall is formed as a series of screens opening size that progressively increases toward a lower end of the cylinder. In FIG. 4, for the sake of simplicity of illustration, only two zones 29a and 29b are shown, but as will be understood, typically the trommel will comprise a number of different zones of progressively increasing screen opening size. For example, a first zone 29a may have holes in the range 2 to 3 inches in transverse dimension and a second zone holes about 4 to about 6 inches in transverse dimension. The drum 29 may be provided with conventional breaking spikes extending inwardly on its inner side in order to break up or shred material passed into the trommel. In use, the solid waste is introduced at the upper end as indicated by the arrow 31 in FIG. 4. The drum 29 is driven by a conventional drive to rotate continuously about its longitudinal axis 30 as indicated by the arrow 30a in FIG. 4. The waste is therefore tumbled within the drum 29 and is subject to the action of the breaking spikes. Small and heavy waste falls through an initial screen such as screen 29a, as indicated by arrow 32 and may pass to a conveyor 33, as seen in FIG. 1, which feeds onto a further conveyor 34. Larger heavy waste falls through the screen 29b, as indicated by the arrow 36 and may be passed by a belt 37 to a shredder 38, the shredded output of which is deposited on the belt 34.

Depending on the composition of the waste, screens that may be intermediate screens 29a and 29b may feed either to the belt 33 or to shredder 38 or may feed to other forms of size reduction apparatus especially adapted for handling materials in the size rankle concerned.

A gas stream is induced to flow inwardly through the perforations of the screens 29a and 29b and downwardly and outwardly through the lower end 39 of the trommel 28.

The gas stream is preferably air, but other gases may, if desired, be employed, for example an inert gas such as nitrogen or carbon dioxide. The gas stream creates a zone of negative pressure relative to the ambient atmosphere at the upper end of the trommel 28 and causes light weight materials, principally paper and plastic, to be retained in the drum 29 without falling out through the perforated portions 29a, 29b and the like, and to be entrained in the gas steam and to exit outwardly through the lower end 39 of the trommel as indicated by the arrow 41 in FIG. 4.

In the case in which, as is usual, the MSW comprises paper, plastics and relatively more dense non-paper non-plastics materials, for example metals and organic materials for example wood or other materials of plant or vegetable origin, the trommel therefore functions to classify the MSW into a dense phase (streams 32 and 36) relatively poor in said paper and plastics and rich in said non-paper non-plastics materials and a light phase (stream 41) relatively poor in said non-paper non-plastics and rich in said paper and plastics.

The gas stream may be induced by blowers 42 arranged to blow obliquely on the outer side of the drum 29 in the region of the screens 29a, 29b, etc., or the stream may be induced by withdrawing gas, for example with a fan, blower or the like, at a zone spaced axially from the lower end 39 of the trommel 28. The paper and plastics material entrained in the stream 41 may be separated. For example, in mid flight the mixture of paper and plastic may be exposed to a hot gas or vapor, for example steam, in order to shrink or collapse the plastic materials to a denser form that tends to segregate laterally from the stream. In the preferred form, as shown in FIG. 1, the stream 41 is passed to a hot drum or other separating device 42 where paper is separated from plastics. The plastics tend to adhere to the drum and is removed by a scraper or the like, while the paper tends to continue through the drum, and is blown by a blower 43 to a paper storage and compaction arrangement comprising for example a negative slope container 44 from which it is removed and compacted in a baler 46 for shipment.

The polyethylene or other plastics removed at the drum 42 are likewise passed to a plastics storage and compaction arrangement comprising for example a negative slope container 47 from which the plastic is compacted at a baler 48 for shipment.

As indicated in FIG. 1, the environment adjacent each of the shredders 24 and 38 and adjacent the paper storage device 44 may be maintained at subatmospheric pressure in order to inhibit emissions of dust. Air may be removed from these regions by lines 11a, 11b and 11c, respectively, feeding through respective blowers 12a to 12c to baghouse filters 13a to 13c, respectively. The dust free air may be exited to the atmosphere by respective blowers 14a to 14c, or may if desired be supplied as combustion air to an adjacent power plant.

Referring again to FIG. 4, the lower portion of the drum 29 adjacent the end 39 may be provided with a magnetic separator arrangement for separating ferrous and like magnetic materials. The separator may provide a magnetic field that is effective around the periphery of the drum except at an upper quadrant thereof. For example, the field applying means may comprise electromagnets connected to the drum 29 that are arranged to switch off when they approach the upper part of the drum's rotation, or may comprise fixed magnets extending around the periphery of the drum except at the upper quadrant, so that ferrous materials and the like are attracted to the inner wall of the drum and are carried upwardly with the drum's rotation and then fall from the inner side of the drum adjacent the upper part of its rotation onto a conveyor 49 that conveys the ferrous materials, to a point indicated by an arrow 51 in FIG. 4 and to a conveyor 52 and a ferrous metals storage and compactor arrangement 53. The heavy waste proceeding along the conveyor 34 is subjected to the action of a magnetic separator 54 which lifts the ferrous or other magnetic materials from the conveyor 34 and passes them to the ferrous metals conveyor 52 to join the stream 51 passing to the storage and compactor arrangement 53.

The remaining, non-magnetic fraction passes to a conveyor 56 on which it may be subjected to the action of conventional eddy current equipment 57 that induces eddy currents in conductive metals remaining in the waste stream, principally aluminum, and repels these materials forcefully laterally from the conveyor 56 onto a conveyor 58 feeding to an aluminum or non-ferrous metals storage and compactor arrangement 59.

The remainder of the waste on the conveyor 56, is mostly organic at this point. For example it may include material of plant or vegetable origin, such as wood, wood fibres, vegetable refuse and the like, and non-vegetable digestible organics. Often, it contains heavy metal contaminant. This material is fed to an anaerobic digester, for example a two stage anaerobic digester arrangement illustrated in FIG. 2 and Ln FIGS. 5 to 8.

Figure 2:
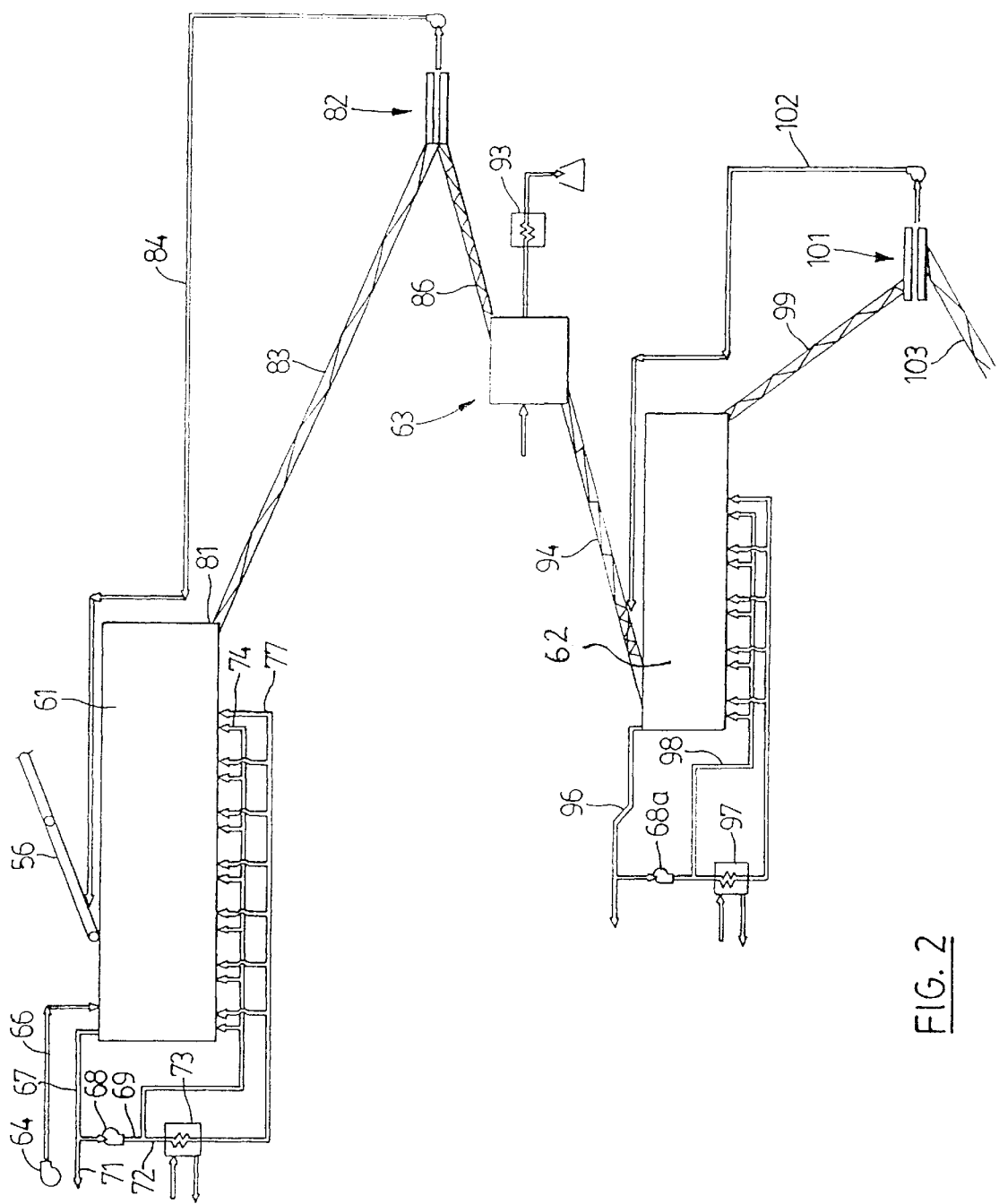

The two stage anaerobic digester illustrated in FIG. 2 comprises anaerobic digesters 61 and 62 for decomposing organic waste to produce digester gas. These digesters effect almost complete digestion of organics (approximately 95% of the organics are digested), thus reducing the need to treat excess liquor. In general, the process involves a two stage anaerobic digestion process, and an organics cooker 63 shown in more detail in FIG. 8. Known designs of digester which applicant is aware involve the use of cylindrical vats with a wall at the middle and a ramp like bottom. These impede the movement of the digestate as it moves from the inlet to the outlet of the digester. Moreover, known designs acid steam at the inlet of the digester to increase the temperature of the feedstock to either mesophilic or thermophilic conditions. The known processes therefore do not offer freedom of temperature control within the digester in the same manner as in the process of the invention. The process of the invention also has the ability, if desired, to remove a mercury content from the organics and yields a stable saleable product.

More specifically, both the primary and secondary digesters 61 and 62 are continuously fed horizontal vats with their bottoms at a slight incline and with no internal, mechanical moving parts. This arrangement allows for a less expensive system and allow the facility to run all year round with minimal or no maintenance work. Furthermore, since the digesters 61 and 62 are horizontal vats, there is free, usually straight line, movement of the digestate or organics from the inlet to the outlet of the digester. Shredded municipal wastes, typically comprising digestible organic material, lignin coated cellulose fiber, and heavy metal contaminant, may be mixed with recirculated digester liquids, leachate from a near by landfill and/or water before entering the digester. Using leachate from a landfill aids in the anaerobic digestion process. As the wastes move through the digester 61 or 62, it is mixed and heated, preferably by recirculated, compressed digester gas. The recirculated digester gas may be heated by any convenient source of heat, for example from the waste heat of the flue gas of an adjacent power plant via a heat exchanger or by use of part of the digester gas as fuel to provide hot gas for a heat exchanger. By controlling the amount of mixing and the temperature at different regions throughout the digester, the digestion of organic wastes may be optimized. The primary digester 61 serves to digest non-fibrous organic waste and some of the fibrous organic waste. The secondary digester 62 serves to completely digest the fibrous organic waste after being passed through an explosion process denoted at 63. This avoids problems of production of excess process water or liquor as encountered in other anaerobic digestion process in Europe and North America.

The explosion stage 63 may be similar to a conventional steam explosion process used in the production of fiberboard, as sold under for example the name MASONITE (trademark) with one major difference: the goal in the present case is to expose the cellulose of lignin-coated cellulose fiber of the fibrous organic waste for further digestion as opposed to stripping the lignin from the cellulose for making fiberboard. Therefore, the explosion process in the present invention may be operated with considerably greater flexibility of choice of the processing pressures and temperatures since the precise temperature and pressure at which explosion occurs is of little importance. As a result of the high pressure and temperature conditions, any mercury that was entrained in the waste exiting digester 61 evolves from a liquid state to a vapor state. The vaporized mercury is mixed with the steam. This gives an opportunity to remove the mercury by condensing the vaporized mercury and steam mixture in a condensing unit. By taking advantage of the difference in density of the two species in the mixture (mercury having the higher density), the mercury can be separated easily. The mercury may be drained first and then the aqueous condensate. Unlike pulping processes used in the pulp and paper industry, further delignification of the fibers is not necessary since the secondary digester 62 will digest the cellulose almost completely leaving the lignin behind. The lignin may then be used as a catalyst for an electrolysis stage of product polishing described in more detail later, or may be left in the aggregate at the end of the process, or may be isolated to be sold.

Figure 5:
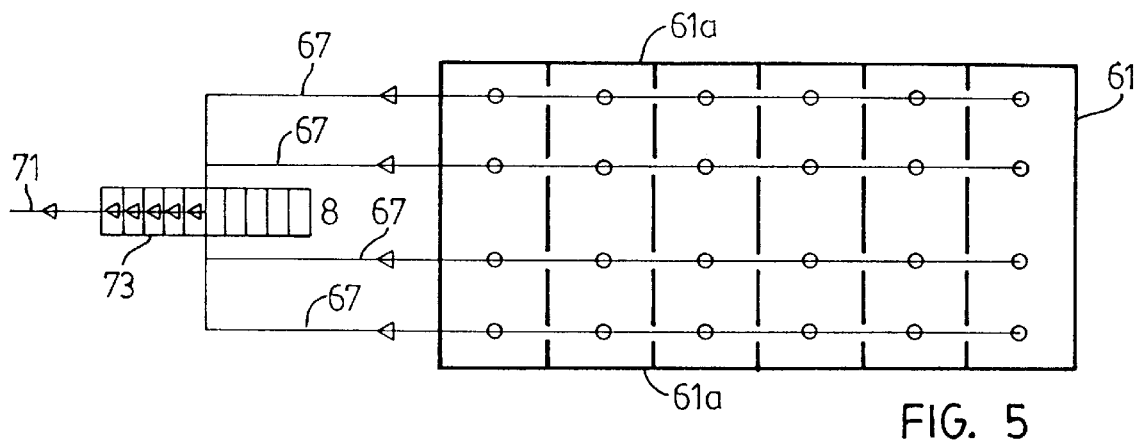
FIGS. 5, 6 and 7 illustrate partially schematically a top plan view, side view and bottom view of preferred forms of digesters in accordance with the invention.
Figure 6:
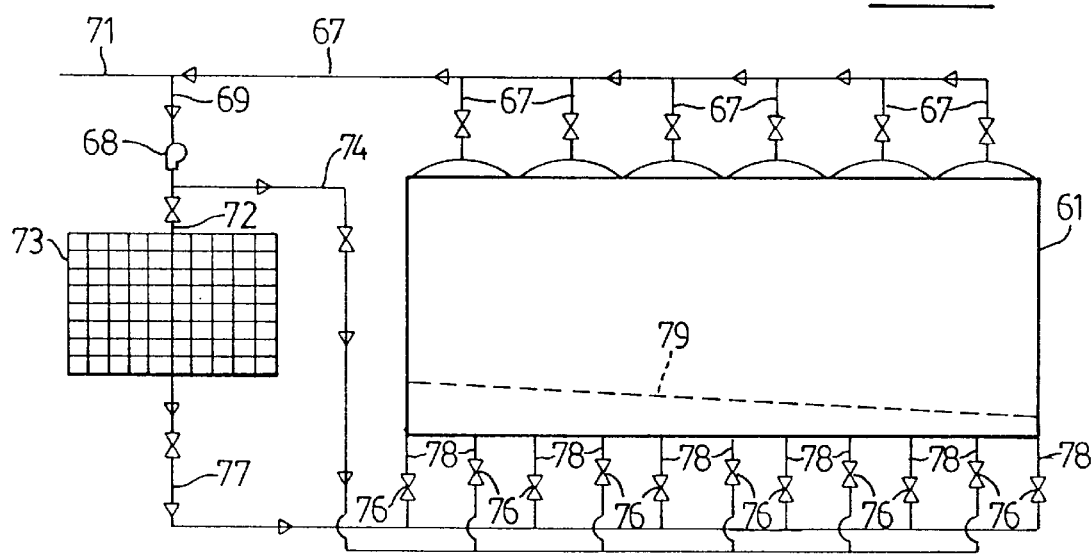
Figure 7:
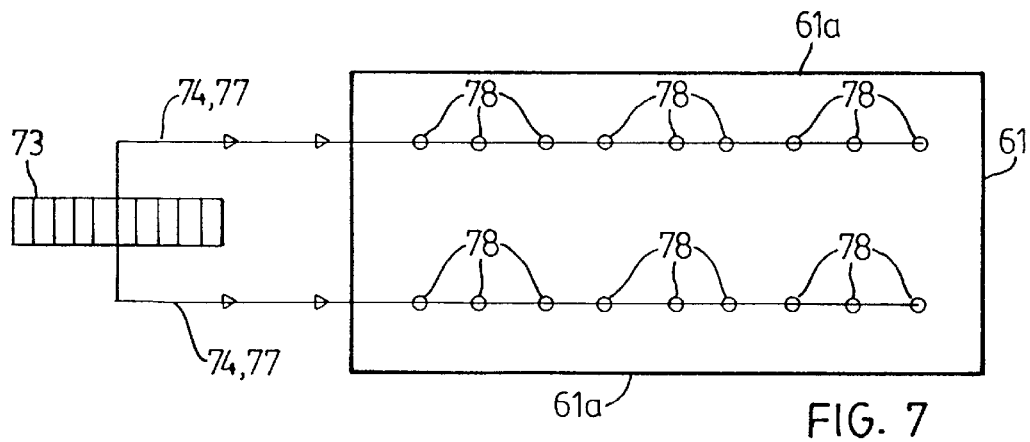

Referring to FIG. 2, the solid waste passing along line 56 from the sorting and reclamation process, which as noted above is mostly organic, is fed to the primary anaerobic digester 61. The waste continuously enters the digester 61 which in the preferred form may be maintained in one or more regions thereof at mesophilic conditions (about 35 to about 40° C.) and in one or more other regions thereof at thermophilic conditions (about 55 to about 60° C.). Liquid enters the digester 61 pumped by a pump 64 along a line 66 at the same point as the waste enters the digester 61 to further aid in the digestion process. Sufficient liquid phase, which may be water, leachate or recirculated digester liquid, is added to form a slurry of the solid waste of the flowable consistency. As shown in more detail in FIGS. 5 to 7, digester gas is collected at the top of the digester 61 along lines 67. While FIGS. 5 to 7 show details of the structure of the digester 61, it will be appreciated the structure of digester 62 is similar. Some of the digester gas collected along lines 67 is recirculated along a line 69 for mixing and heating while the bulk passed alone a line 71 is either used as fuel in a power plant or stored for some other utilization. The recirculated gas passes through a compressor 68 to allow for easier mixing. A controlled quantity of the recirculated gas passes along a line 72 through a heat exchanger 73 in which any conveniently available heating medium is used to heat the gas typically to a temperature of about 55 to about 60° C. In the case where the process is used in combination with a power plant this medium may be flue gas. The remainder of the recirculated gas bypasses the heat exchanger along line 74.

By use of control valves 76, the ratio of heated gas passed along line 77 and unheated gas from line 74 entering each region of the digester 61 can be regulated and controlled and hence the temperature of each region can be controlled to promote establishment and maintenance of different bacterial domains, for example, thermophilic and mesophilic regions throughout the digester 61 to optimize digestion. Further the flows through the inlets 78 and passing upwardly through a pervious inclined bottom 79 are controlled to control the fluidization of the waste slurry and hence control flow rates and retention times in digester 61. Hence, for a given consistency of the slurry in the digester 61, and a given slope or angle of the bottom 79, the rate of flow of the slurry through the digester 61, and the residence time in the digester, can be controlled by controlling the flow of gas upwardly through the inlets 78. The angle of the bottom 79 with respect to the horizontal is preferably about 0.2 to about 0.4 degrees.

Waste exits the digester at 81 and enters a solid-liquid separator for example a press 82 along line 83 that captures digester liquor which is recirculated by line 84 to the front of the digester. By recirculating the digester liquor, the heat needed in the explosion stage 63 is reduced.

As noted above, the primary digester 61 only digests the exposed cellulose and not fibrous waste coated with lignin. As shown in more detail in FIG. 8, the solid phase of the waste from separator 82 passes along line 86 through a compressor 87 to an explosion drum 88 shown in more detail in FIG. 8. Compression of the waste serves to facilitate continual operation of the drum 88. The compressed material is then injected into the drum 88. The contents of the drum 88 are heated and pressurized sufficiently to provide adequate exposure of cellulose fiber on subsequent explosive decompression. Preferably a saturated steam pressure of about 100 to about 1000 psia is attained, corresponding to a temperature of about 150 to about 300° C. The heating and pressurization may be effected by steam that enters the drum 88 at elevated pressure and temperature along line 89 and serves to pressurize the drum 88 and its contents to the required pressure. In one form, superheated steam at a temperature about 300 to about 500° C., more preferably about 400° C. and at a pressure preferably in excess of about 800 psia is supplied through the line 89.

Alternatively, instead of direct steam heating, indirect heating may be employed. Usually, the incoming material is sufficiently wet that when it is heated indirectly, for example by heating applied to the exterior of a pipe containing the waste, and that forms the core of the drum 88, in the presence of moisture the indirect heating boils the moisture in the MSW to raise pressure required for the desired explosive decompression. It has been found that the explosion is more effective in liberating lignin-coated fibers when the. MSW prior to decompression is at a relatively low moisture content.

Once the pressure has reached the required level all inlets to the drum 88 are closed and a valve 91 is opened at the bottom of the drum dumping the contents into a flash tank 92 and causing an explosion which serves to break up the fibrous organics and expose the cellulose interior thus allowing digestion of the exposed fiber.

If desired, in the case in which the MSW contains mercury, in an initial stage of the heating of the MSW in drum 88, a valve 90 is opened, allowing steam and other vapors to exit the drum 88 and pass through one or more condensers 93 so that mercury evolved in the manner described earlier may be recovered. The condensate from the condensers 93 is allowed to stand so that separate layers of water and liquid mercury settle out. The lower layer of liquid mercury is periodically bled off by opening valves 93a and is recovered. The water recovered separately may be returned to digester 61. This initial stage of heating may be continued until the batch of material in the drum 88 is substantially mercury free, and may, of course, be omitted in the case in which the MSW has no significant mercury content requiring decontamination. The valve 90 is closed before the valve 91 is opened. The waste from flash tank 92 is transported by a conveyor 94 to the secondary digester 62. The remaining organic waste is digested in the secondary digester 62 in almost the same manner as described above for the primary digester 61. That is, the digester gas is collected off the top of the digester 62 along line 96 and some is recirculated through a heat exchanger 97 to be used for heating and mixing the digestate and some is directed along line 98 only for mixing. The remaining waste exits the digester 62 along line 99 and consist of mainly inerts with a small amount of undigested organics, including lignin, and an even smaller amount of plastics and heavy metals. The waste passes through a separator such as press 101 to recover digestate liquor which is recirculated to the front of the digester 62 by line 102.

As shown in FIGS. 5 to 7, both anaerobic digesters 61 and 62 are preferably rectangular in shape having the appropriate dimensions for handling the incoming feedstock for the digester. Since the shape of the digester is rectangular, and the side walls 61a guide the slurry in the digesters 61 and 62 in a substantially straight line path from their inlets to their outlets, there is no hindrance to the flow of the digestate. Gas compressors 68 and 68a ensure that the pressure required to overcome the head of the digestate in digesters 61 and 62 is achieved.

While the above description provides ample information to enable one of ordinary skill in the art to carry out the process, for the avoidance of doubt some examples of specific conditions will be given. In one preferred form the retention time is approximately 20 days for each of the digesters 61 and 62. The digester pH is preferably maintained at approximately 7 by addition of conventional buffering agents as necessary. The organics digested in the first digester 61 amount to about 50% of the incoming organic mass, and the organics digested in the second digester 62 amount to about 90% of the incoming mass, so that the combined digestion amounts to about 95% of the total organic waste. An energy, input of about 66000 Btu/tonne (metric ton) hour is required for each of the digesters 61 and 62 to heat them to thermophilic conditions (approx. 55° C.) based on the weight of the material supplied along the lines 56 and 94, respectively. The gas compressors 68 and 68a compress the recirculated gas to preferably about 15 to 150 psia to facilitate mixing of the waste in the digester. This increased pressure aids in transport of the digester gas.

In the explosion stage 63, the processing time of each batch in the drum 88 is about 1 to 2 minutes, and the heating requirements to raise the temperature and pressure inside the drum 88 to attain a saturated steam pressure in the region of 800 to 1200 psia amounts to about 1 MBtu/tonne hour, based on the weight of the feed along line 86.

The solid phase of the digestate from digester 62 separated at separator 101 comprises inert materials, undigested organic material including lignin, some plastics materials and a small content of heavy metals. In a preferred form this solid phase is passed along a line 103 to a product polishing and heavy metal recovery stage shown in FIG. 3.

Generally, in known processes of anaerobic digestion of solid wastes, the end product of the digestion although often referred to as compost, is not suited for use as agricultural compost because of its heavy metal concentrations and the digester product has often had to be landfilled.

One form of the process, described below, solves this problem by creating a stable aggregate which can be utilized as an inert filler, as aggregate for concrete making, horticultural purposes, or for other similar uses.

This form of the process allows for a profitable, continuous recovery of heavy metals and at the same time recovers other valuable resources from anaerobically digested solid waste. The heavy metals are removed from the aggregate by dissolving them in an inorganic or mineral acid solution in an acid tank 104 at which point plastics may also be recovered. The metals are then electrolytically plated out of the acid solution in a separate tank in which undigested lignin is utilized to produce a purer plated metal. By utilizing sulfuric acid or hydrochloric acid as the mineral acid or acids the process has the ability to recover most heavy metals including: Sn, Mo, Ni, Cu, Pb, Zn, Cd, and Cr.

Figure 3:
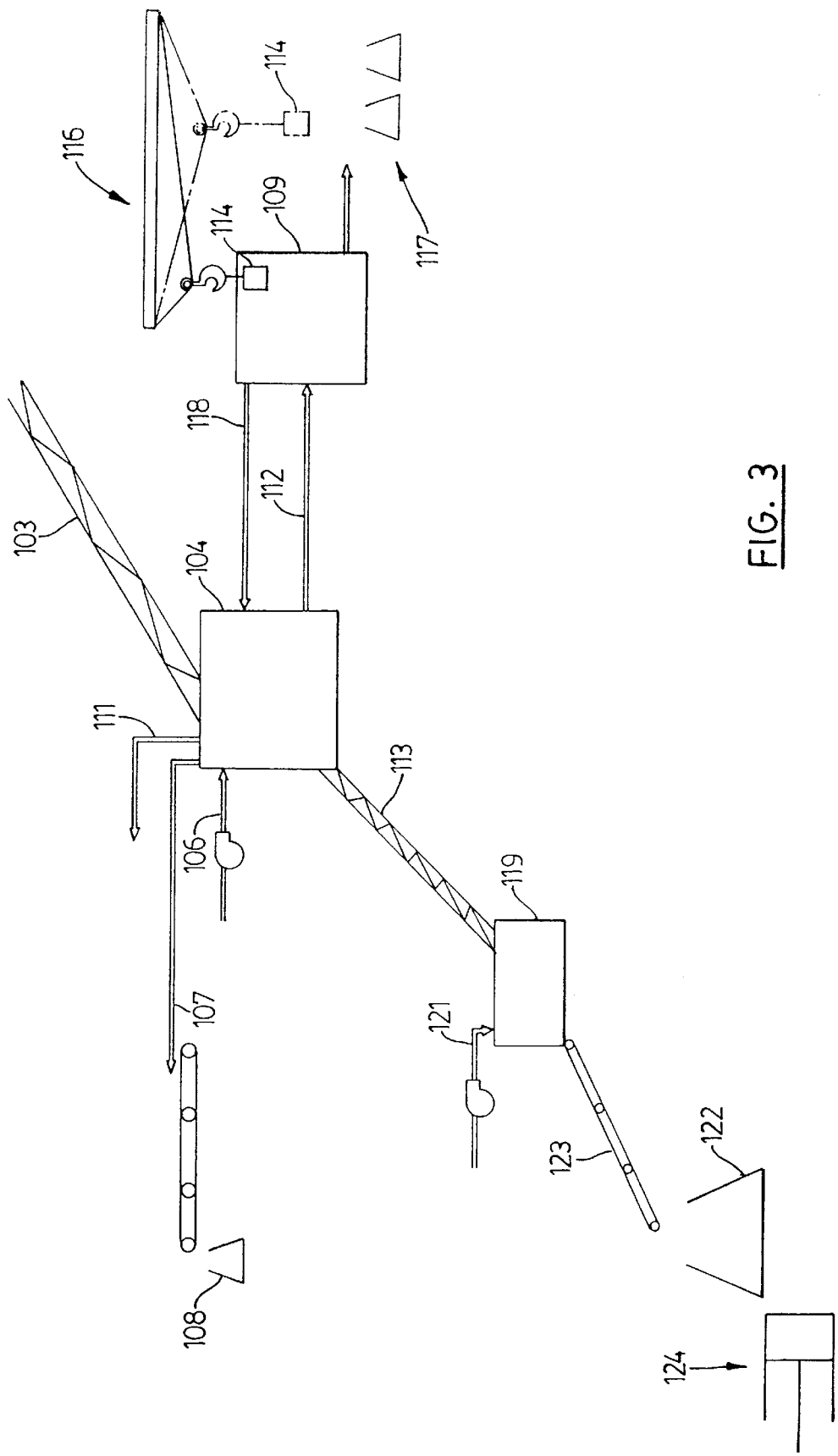

As shown in FIG. 3, the solids portion of digested waste, from which excess moisture has been previously removed in press 101, so that acid concentrations can be maintained at a sufficiently high level, enters the acid tank 104. This waste may have a concentration of heavy metals in the range of 5 to 10 percent of the total mass. The acid tank 104 is made of a corrosion resistant material and contains mineral acid solution, preferably sulfuric acid with a concentration of approximately 50 percent, or hydrochloric acid. Sulfuric acid is preferably used for reasons of economy while hydrochloric acid may be required to dissolve metals, if present, which are otherwise insoluble in sulfuric acid, such as lead. Since some of the acid is lost during the process, either as hydrogen gas and hydrogen sulphides, or is bound up physically in the aggregate, or by reduction in concentration due to the addition of water with the digested waste, and to make up this loss new acid is added through line 106 as need be in order to maintain the desired concentration. This solids waste entering the tank is mixed with the acid solution to yield a heavy metal salt solution containing heavy metal cations and lignin in solution. Desirably, the specific gravity of the solution in the tank 104 is maintained in the range about 1.0 to about 1.4, usually in the range of the specific gravities of concentrated hydrochloric acid (1.2) and 50% sulfuric acid (1.4). As a result, when the waste enters the acid tank 104 light materials float to the top. These materials include most plastics and undigested organics. The light materials, mostly plastics, are skimmed from the surface of the tank 104 and passed along line 107 to storage 108. As the digested waste is added to the acid tank 104 hydrogen gas and hydrogen sulphides form due to several reactions: volatile organics can be destroyed and the metal—acid reaction produces hydrogen gas. Preferably, the tank 104 is pressurized to keep hydrogen in solution in the acid tank to allow later regeneration of acid in the electrolysis tank 109. Hydrogen that escapes is collected along line 111 and either is used as a fuel in a gas power plant or is returned to the electrolysis tank 109.

In one form, the tank 104 is operated on an intermittent basis. For example the tank 104 may be loaded with waste during a day time operating shift while the recycling plant is operated and the waste is left in contact with the acid overnight and the acid solution containing dissolved metal salts drawn off along line 112. The depleted solid waste comprising an insoluble residue is exited along line 113 before recommencing filling the tank with waste and acid. Alternatively, the tank 104 may if desired operate continuously with countercurrent flow of acid and waste. In such case, the spent acid freed from solid waste and relatively rich in heavy metal salts is passed along line 112 to the electrolysis tank and the barren waste freed from liquid acid may, be passed along line 113. Any conventional countercurrent solid-liquid treatment scheme may be adopted for this purpose.

The acid salt solution passed along line 112 contains lignin from the digested waste stream and this aids in the plating process. The electrolysis tank 109 is made of a corrosion resistant and electrically insulating material. Large plates of appropriate metals are suspended in the solution in the tank and large electrical currents (roughly 100 kA per tonne metal to be deposited) are passed through the tank to ensure maximum plating of the metals. The plates of metal 114 are removed from the tank by crane 116 or similar device and placed in storage 117. As the metals are plated out of the solution acid is regenerated from dissolved hydrogen at the anode and is returned to the acid tank 104 along line 118.

When the use of more than one mineral acid is required, for example hydrochloric acid is required to dissolve lead in a batch of waste containing appreciable lead values, it is not always possible to use a mixture of acids since hydrochloric acid, for example, reacts with concentrated sulfuric acid to produce chlorine. In such case, after treatment with one acid, for example sulfuric acid as described in detail above, the depleted solid waste may be washed to free it from sulfuric acid, pressed or otherwise subjected to a liquids/solids separation to free it from liquid phase and then the above procedure described above in detail with reference to FIG. 3 is repeated using hydrochloric acid as the mineral acid solution in the tank 104.

The digested waste or aggregate, now free of nearly all heavy metals, with a concentration of heavy metals in the range of 0.05 to 0.1 percent of mass, exits the acid tank along line 113. The aggregate is acidic in nature and needs further processing to rebalance its pH. This takes place in a neutralizing tank 119 where the aggregate is mixed with calcium carbonate or other base fed through line 121. The pH is monitored to control addition of the base and ensure maximum efficiency of the neutralization. From here the aggregate is put into storage 122 along line 123, and may be compacted at 124 for shipping.

While the above provides ample information to enable the skilled reader to operate the process, for the avoidance of doubt some specific examples of operating conditions are given.

The average electrical power requirements for electrolysis in tank 109 are typically 0.5 MW/tonne of recovered heavy metals in the case in which the process is run 24 hours per day. The typical surface area of the metal plates in the electrolysis tank 109 is 5000 sq. ft./tonne of metal to be deposited. The pH in tank 104 is preferably maintained at 5.

In one example of operation of the process as described above with reference to FIG. 3, a maximum of about 1 tonne of acid is consumed for every 50 tonnes of waste passed along line 103 while 1 tonne of base/25 tonnes of waste, based on the weight of barren waste fed along line 113, is typically used to neutralize the acid.

Various modifications may of course be made to the procedures described above in detail.

Figure 8:
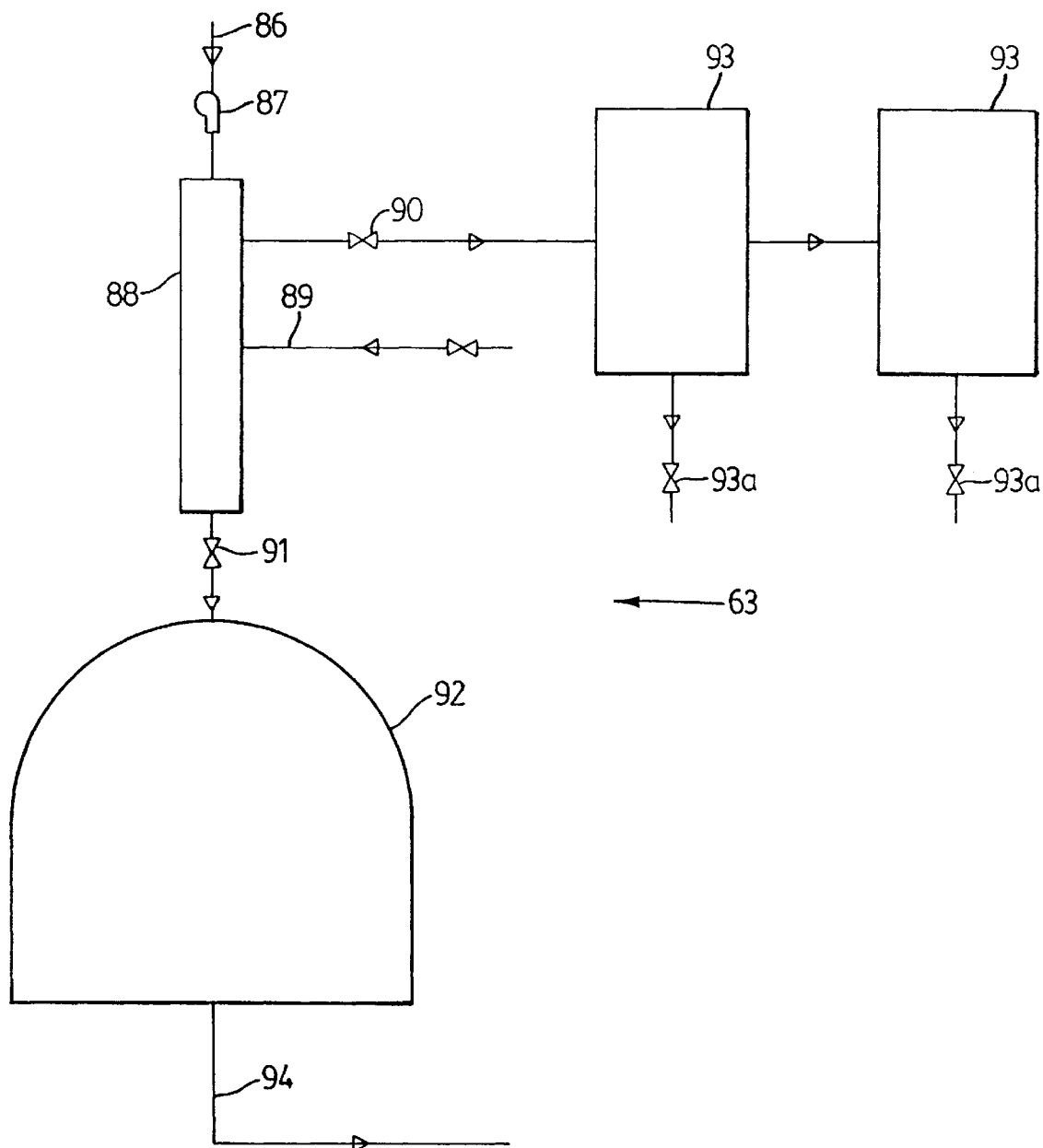
FIG. 8 shows somewhat schematically in the nature of a flow diagram a preferred form of steam explosion apparatus in accordance with the invention.

For example, instead of subjecting the MSW to two stages of anaerobic digestion with an intermediate explosive decompression stage, explosive decompression may be performed before digestion is conducted. This may provide improved efficiency of waste corversion, especially, for example where the material to be digested contains a significant quantity of lignin-coated cellulose fiber material. In such case, the principally organic waste stream from conveyor 56 with the addition if necessary of an aqueous phase if required to reach a desired moisture content, may be fed direct to the line 86 as seen in FIG. 8 that supplies the compressor 87 feeding the drum 88. The output stream 97 from the flash tank 94 is fed to a digester such as digester 62.

In one preferred form, heavy metal removal from the aqueous phase is conducted during digestion. This procedure is illustrated in more detail in FIG. 9. In many instances, the anaerobic digestion process, owing to its generally reducing character, tends to promote the formation of inert and non-leachable complexes of heavy metals with organics present in the digestate. In such case, the non-leachable complexes can be left in the digestate to form part of the final undigested compost since they may be safely disposed of. In other cases the aqueous phase in the, or each, digester may contain heavy metal ions in soluble form and in such case it is presently preferred to remove such heavy metal ions by withdrawing a portion of the aqueous phase prior to the completion of the digestion and treating the aqueous phase to remove heavy metal ions therefrom. In this manner, the efficiency of the operation is improved since heavy metal ion removal can proceed during the course of the digestion.

Figure 9:
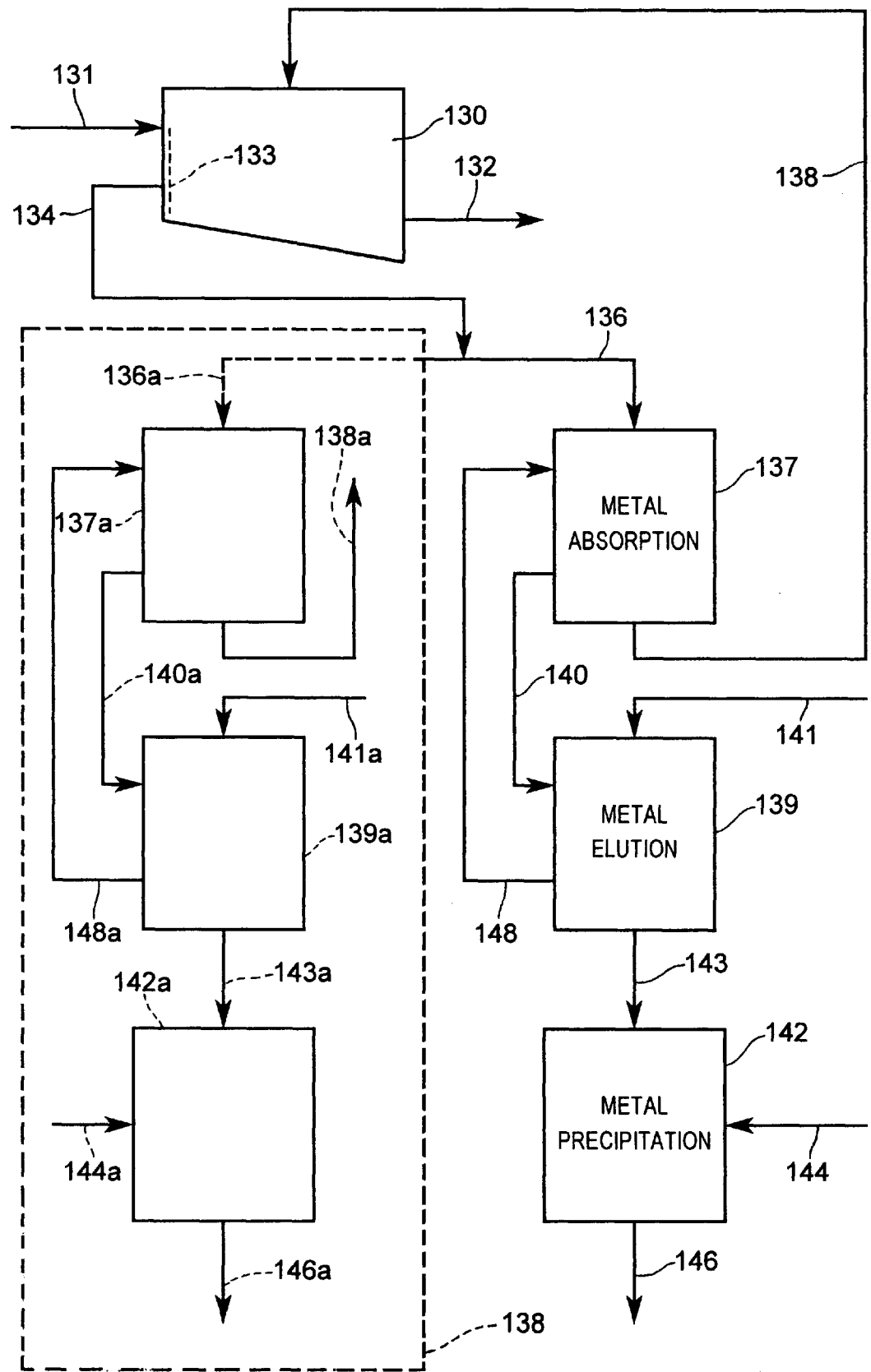
FIG. 9 shows an example of apparatus for removal of heavy metals from the aqueous phase of the digester contents.

Referring to FIG. 9, this shoes a digester 130, generally constructed and operated similarly to digesters 61 and 62 as described above in detail with reference to FIGS. 2 and 5 to 7.

The digester 30 may be the sole digester in the MSW conversion process or may be a primary or secondary digester in a two stage digestion process and may or may not be preceded by an explosive decompression stage.

Incoming MSW, or partly digested material, is fed along inlet line 131 and has an aqueous phase content sufficient to impart a flowable slurry consistency. Digestate slurry exits on line 132. A portion of the aqueous phase, separated from the solids phase by a screen 133 is withdrawn along line 134 and is subjected to a heavy metals removal procedure that removes one or more, or, more usually, all of the following heavy metals, when present: Sn, Mo, Ni, Cu, Pb, Zn, Cd, Hg and Cr. Any conventional metal ion removal technique may be used, such as the use of reverse osmotic pressure membranes, separation membranes, or chemical precipitation. These techniques are well understood by those skilled in the art and need not be described in detail. The heavy metal ion poor aqueous phase may be recycled to the digester, utilized to slurry incoming solids along line 131, or may be discarded.

In a preferred form, a regenerable solid adsorbent, such as activated carbon, or solid non-water soluble particulate adsorbent containing metal adsorption sites, for example, a cation exchange resin, is employed. Again, these techniques are well understood by those skilled in the art and need not be described in detail. Merely by way of illustration, in FIG. 3, the heavy metal ion bearing liquid phase is fed along line 136 and flowed through an ion exchange resin column 137 that adsorbs heavy metal ions therefrom. The barren liquor is recycled to the digester 130 along line 138. Once the resin in column 137 approaches saturation, but before break through of heavy metal ion occurs, the flow along line 134 is switched along line 136a to an auxiliary adsorption column 137a forming part of an auxiliary adsorption-regeneration circuit denoted as a whole at 138, and that mirrors the circuit of which the first mentioned column 137 forms part, and flow along line 136 is ceased. While column 137a undertakes heavy metal ion adsorption and barren liquor is recycled to digester 130 along line 138a, the metal laden resin in column 137 is regenerated by slurrying it to an election column 139 along a line 140 and a regenerant solution or metal elution reagent, for example 2N HCl in the case in which the solid adsorbent is a cation exchange resin, supplied along line 141, is flowed through the resin particles. The eluate is routed to a metal precipitation vessel 142 along line 143 where it is reacted with a solution, for example caustic soda or sodium sulfide supplied along line 144, that precipitates the metals to form a metal precipitate waste product 146. After rinsing with fresh water, the metal eluted generated adsorbent in returned to the adsorption column 137 along a line 148, and flow along the line 136 is recommenced. The depleted resin in column 137a is then regenerated in a manner similar to that described above in detail for the resin in column 137. The elements 138a to 148a of circuit 138 function similarly to elements 138 to 148 as described above. The metal adsorption and elution steps may of course be performed in the same vessel by use of appropriate valuing and by rinsing between the steps of adsorption, elution and re-use for adsorption. Rinsing may be conducted with fresh water.

We claim:

1. A method of digestion of municipal solid waste (MSW) comprising digestible organic material and lignin coated cellulose fibers, comprising: heating said MSW in the presence of moisture to yield a heated solid phase; elevating the ambient pressure of and then explosively decompressing the heated solid phase to yield a treated solid phase comprising at least a substantial portion of the fibers in a ruptured condition exposing the cellulosic internal surfaces thereof; slurrying the treated solid phase in an aqueous phase; subjecting the slurry to at least one stage of anaerobic digestion to yield a digested solids slurry; and separating a substantial portion of the aqueous phase from the digested solids slurry to yield a digested solids residue.

2. A method as claimed in claim 1 wherein said at least one stage of anaerobic digestion comprises passing said slurry through a digester having a pervious bottom wall inclining downwardly from an inlet end to an outlet end, and maintaining and regulating a temperature in said slurry elevated above ambient temperature by supplying through said pervious bottom wall a regulated mixture of a gas heated to above ambient temperature and a non-heated gas.

3. A method as claimed in claim 2 wherein said heated and non-heated gas each originates with gases withdrawn from an upper region of the digester.

4. A method as claimed in claim 3 wherein at least one region of the slurry in the digester is maintained at a mesophilic temperature condition of about 35 to about 40° C. and a second region of the slurry in the digester is maintained at a thermophilic temperature condition of about 55 to about 60° C.

5. A method as claimed in claim 3 wherein said pervious bottom wall inclines at an angle of bout 0.2 to about 0.4 degrees with respect to the horizontal.

6. A method as claimed in claim 1 wherein said at least one stage of anaerobic digestion is conducted in a digester comprising side walls guiding said slurry for flow in a substantially straight line path between an inlet end and an outlet end.

7. A method as claimed in claim 1 wherein the heated solid phase is elevated to a saturated steam pressure of about 100 to about 1000 psia before it is explosively decompressed.

8. A method as claimed in claim 1 wherein said at least one stage of anaerobic digestion digests about 50% to about 90% of its incoming organic mass.

9. A method as claimed in claim 1 wherein said MSW comprises heavy metal contaminant, and including the steps of withdrawing a portion of the aqueous phase from said slurry before completion of said at least one stage of anaerobic digestion, said aqueous phase containing one or more dissolved heavy metals; removing one or more heavy metals from said aqueous phase to yield a heavy metal poor aqueous phase and discarding said heavy metal poor aqueous phase or utilizing said heavy metal poor aqueous phase as an aqueous phase used for slurrying said treated solid phase.

10. A method as claimed in claim 9 wherein said one or more heavy metals comprises one or more of Sn, Mo, Ni, Cu, Pb, Zn, Cd, Hg and Cr.

11. A method as claimed in claim 9 wherein said step of removing one or more heavy metals from said aqueous phase comprises conducting said aqueous phase with a heavy metal adsorbent comprising water insoluble particles containing metal adsorption sites; allowing said absorption sites to adsorb one or more heavy metals thereon and thereby form said heavy metal poor aqueous phase; and separating said heavy metal poor aqueous phase from said adsorbent.

12. A method as claimed in claim 1 wherein said digested solids residue comprises lignin and heavy metals, and including the step of mixing said residue with mineral acid solution to solubilize at least some of said heavy metals and yield an insoluble residue and a heavy metal salt solution comprising heavy metal cations and lignin subjecting the solution to electrolysis and causing electrodeposition of said cations in the presence of said lignin to yield a heavy metal electrodeposit, and recovering the electrodeposit.

13. A method of digestion of municipal solid waste (MSW) comprising digestible organic material and lignin coated cellulose fiber, comprising: slurrying said MSW in an aqueous phase; subjecting the slurry to a primary stage of anaerobic digestion to digest at least a substantial portion of the organic material; separating aqueous phase to yield a primary solid digested residue; heating the primary solid residue in the presence of moisture to yield a heated solid phase; elevating the ambient pressure of and then explosively decompressing the heated solid phase to yield a treated solid phase comprising the fibers in ruptured condition exposing the cellulosic internal surfaces thereof; slurrying the treated solid phase in an aqueous phase and subjecting the slurry to a secondary stage of anaerobic digestion; and recovering a secondary solid digested residue.

14. A method as claimed in claim 13 wherein at least one of said steps of subjecting the slurry to a primary stage of anaerobic digestion and subjecting the slurry to a secondary stage of anaerobic digestion comprises passing said slurry through a digester having a previous bottom wall inclining downwardly from an inlet and to an outlet end, and maintaining and regulating a temperature in said slurry elevated above ambient temperature by supplying through said pervious bottom wall a regulated mixture of a gas heated to above ambient temperature and a non-heated gas.

15. A method as claimed in claim 14 wherein said heated and non-heated gas each originate with gases withdrawn from an upper region of the digester.

16. A method as claimed in claim 14 wherein at least one region of the slurry in the digester is maintained at a mesophilic temperature condition of about 35 to about 40° C. and a second region of the slurry in the digester is maintained at a thermophilic temperature condition of about 55 to about 60° C.

17. A method as claimed in claim 14 wherein said pervious bottom wall inclines at an angle to about 0.2 to about 0.4 degrees with respect to the horizontal.

18. A method as claimed in claim 13 wherein at least one of said primary and secondary stages is conducted in a digester comprising side walls guiding said slurry for flow in a substantially straight line path between an inlet end and an outlet end.

19. A method as claimed in claim 13 wherein the heated phase is elevated to a saturated steam pressure of about 800 to about 1200 psia before it is explosively decompressed.

20. A method as claimed in claim 13 wherein said primary stage digests about 50% the incoming organic mass and said second stage digests about 90% of its incoming organic mass.

21. A method as claimed in claim 13 wherein said MSW comprises a heavy metal contaminant, and including the steps of withdrawing a portion of the aqueous phase from said slurry before completion of at least one stage selected from said primary and secondary stages of anaerobic digestion, said aqueous phase containing one or more dissolved heavy metals; removing one or more heavy metals from said aqueous phase to yield a heavy metal poor aqueous phase and discarding said heavy metal poor aqueous phase or utilizing said heavy metal poor aqueous phase as an aqueous phase used for slurrying a solid phase in said at least one stage.

22. A method as claimed in claim 21 wherein said one or more heavy metals comprises one or more of Sn, Mo, Ni, Cu, Pb, Zn, Cd, Hg and Cr.

23. A method as claimed in claim 21 wherein said step of removing one or more heavy metals from said aqueous phase comprises conducting said aqueous phase with a heavy metal adsorbent comprising water insoluble particles containing metal adsorption sites; allowing said adsorption sites to adsorb one or more heavy metals thereon and thereby form said heavy metal poor aqueous phase; and separating said heavy metal poor aqueous phase from said adsorbent.

24. A method of digestion and decontamination of municipal solid waste (MSW) comprising digestible organic material, lignin coated cellulose fiber, and mercury contaminant, comprising: slurrying said MSW in an aqueous phase; subjecting the slurry to a primary stage of anaerobic digestion to digest at least a substantial portion of the organic material; separating aqueous phase to yield a primary solid digested residue; heating the primary solid residue in the presence of moisture to yield a water and mercury vapor containing vapor phase and a substantially mercury free heated solid phase; collecting the vapor phase separately from the heated solid phase and condensing the vapor phase to yield water and mercury in liquid form; elevating the ambient pressure of and then explosively decompressing the heated solid phase to yield a treated solid phase comprising the fibers in ruptured condition exposing the cellulosic internal surfaces thereof; slurrying the treated solid phase in an aqueous phase and subjecting the slurry to a secondary stage of anaerobic digestion; and recovering a secondary solid digested residue.

25. A method as claimed in claim 24 wherein at least one of said steps of subjecting the slurry to a primary stage of anaerobic digestion and subjecting the slurry to a secondary stage of anaerobic digestion comprises passing said slurry through a digester having a previous bottom wall inclining downwardly from an inlet end to an outlet end, and maintaining and regulating a temperature in said slurry elevated above ambient temperature by supplying through said pervious bottom wall a regulated mixture of a gas heated to above ambient temperature and a non-heated gas.

26. A method as claimed in claim 25 wherein said heated and non-heated gas each originate with gases withdrawn from an upper region of the digester.

27. A method as claimed in claim 25 wherein at least one region of the slurry in the digester is maintained at a mesophilic temperature condition of about 35 to about 40° C. and a second region of the slurry in the digester is maintained at a thermophilic temperature condition of about 55 to about 60° C.

28. A method as claimed in claim 23 wherein said pervious bottom wall inclines at an angle to about 0.2 to about 0.4 degrees with respect to the horizontal.

29. A method as claimed in claim 24 wherein at least one of said primary and secondary stages is conducted in a digester comprising side walls guiding said slurry for flow in a substantially straight line path between an inlet end and an outlet end.

30. A method as claimed in claim 24 wherein the heated solid phase is elevated to a saturated steam pressure of about 800 to about 1200 psia before it is explosively decompressed.

31. A method as claimed in claim 24, including allowing the water and mercury in liquid form to stand to form a lower mercury layer and withdrawing the mercury layer separately from the water.

32. A method as claimed in claim 24 wherein said primary stage digests about 50% the incoming organic mass and said second stage digests about 90% of its incoming organic mass.

33. A method as claimed in claim 24 wherein said MSW comprises heavy metal contaminant, and including the steps of withdrawing a portion of the aqueous phase from said slurry before completion of at least one stage selected from said primary and said second stages of anaerobic digestion, said aqueous phase containing one or more dissolved heavy metal; removing one or more heavy metals from said aqueous phase to yield a heavy metal poor aqueous phase and discarding said heavy metal poor aqueous phase or utilizing said heavy metal poor aqueous phase as an aqueous phase used for slurrying a solid phase in said at least one stage.

34. A method asa claimed in claim 33 wherein said one or more heavy metals comprises one or more of Sn, Mo, Ni, Cu, Pb, Zn, Cd, Hg and Cr.

35. A method as claimed in claim 33 wherein said step of removing one or more heavy metals from said aqueous phase comprises conducting said aqueous phase with a heavy metal adsorbent comprising water insoluble particles containing metal adsorption sites; allowing said adsorption sites to adsorb one or more heavy metals thereon and thereby form said heavy metal poor aqueous phase; and separating said heavy metal poor aqueous phase from said adsorbent.

* * * * *